United States Patent
Thompson et al.

(10) Patent No.: US 10,065,918 B2
(45) Date of Patent: *Sep. 4, 2018

(54) POLYOL ESTOLIDES AND METHODS OF MAKING AND USING THE SAME

(71) Applicant: BIOSYNTHETIC TECHNOLOGIES, LLC, Irvine, CA (US)

(72) Inventors: Travis Thompson, Anaheim, CA (US); Jeremy Forest, Honolulu, HI (US); Marlon Lutz, Grayslake, IL (US)

(73) Assignee: Biosynthetic Technologies, LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,112

(22) Filed: Mar. 15, 2017

(65) Prior Publication Data

US 2017/0247316 A1     Aug. 31, 2017

Related U.S. Application Data

(63) Continuation of application No. 14/977,361, filed on Dec. 21, 2015, now Pat. No. 9,611,212, which is a continuation of application No. PCT/US2014/045797, filed on Jul. 8, 2014.

(60) Provisional application No. 61/844,276, filed on Jul. 9, 2013.

(51) Int. Cl.
| | |
|---|---|
| C07C 59/00 | (2006.01) |
| C07C 69/67 | (2006.01) |
| C10M 105/36 | (2006.01) |
| A23D 9/00 | (2006.01) |

(52) U.S. Cl.
CPC .............. C07C 69/67 (2013.01); A23D 9/00 (2013.01); C10M 105/36 (2013.01); C10M 2207/2825 (2013.01)

(58) Field of Classification Search
CPC ................................................... C07C 69/67
USPC ......................................................... 554/122
See application file for complete search history.

(56) References Cited

U.S. PATENT DOCUMENTS

| | | | |
|---|---|---|---|
| 2,652,410 A | 9/1953 | Cunningham et al. |
| 2,961,406 A | 11/1960 | McNeil |
| 3,148,147 A | 9/1964 | Alan et al. |
| 5,306,788 A | 4/1994 | Uchida et al. |
| 6,018,063 A | 1/2000 | Isbell et al. |
| 7,581,511 B2 | 9/2009 | Mardian et al. |
| 8,349,930 B2 | 1/2013 | Nielsen et al. |
| 8,846,793 B2 | 9/2014 | Wiebe et al. |
| 2011/0263885 A1 | 10/2011 | Korlipara et al. |
| 2013/0005936 A1 | 1/2013 | Cramail et al. |

OTHER PUBLICATIONS

Haas T., et al., "New Diol Processes: 1, 3-propanediol and 1, 4-butanediol", Applied Catalysis A: General, Elsevier Science Amsterdam, NL, vol. 280, No. 1 Feb. 25, 2005, 83-88.
Harry-O Kuru, et al., "Syntheses of Estolide Esters from cis-9-Octadecenoic Acid Estolides", JAOCS, vol. 78, No. 3 (2001), 219-223.
Isbell, T. , "Chemistry and physical properties of estolides", United States Department of Agriculture, Agriculture Research Service, National Center for Agricultural Utilization Research., Aug. 20, 2011, 1-14.
Kiatsimkul, et al., "Preparation of High Hydroxyl Equivalent Weight Polyols from Vegetable Oils", Industrial Crops and Products 27 (2008), 257-264.
Li, et al., "Heteropolacid Salts as Self-Separation and Recyclable Catalysts for Transesterification of Trimethylolpropane", Applied Catalysis A: General 392 (2011), 233-237.
Uosukainen, et al., "Transesterification of Trimethylolpropane and Rapeseed Oil Methyl Ester to Environmentally Acceptable Lubricants", JAOCS Ed. 2, vol. 75. No. 11 Jan. 1998, 1558.
Wilson et al., "Human Studies on Polyglycerol Polyricinoleate (PGPR)," Food and Chemical Toxicology, 36: 743-745 (1998).
Kunduru et al., "Castor Oil-Based Biodegradable Polyesters," Biomacromolecules, 16: 2572-87 (2015).
Howes et al., "The Fate of Ingested Glyceran Esters of Condensed Castor Oil Fatty Acids [Polyglycerol Polyricinoleate (PGPR)] in the Rat," Food and Chemical Toxicology, 36: 719-738 (1998).
Bastida-Rodriguez et al., "The Food Additive Polyglycerol Polyricinoleate (E-476): Structure, Applications, and Production Methods," ISRN Chemical Engineering, vol. 2013, Article ID 124767, 21 pages, http://dx.doi.org/10.1155/2013/124767.
International Search Report for Application No. PCT/2014/045797 dated Jul. 8, 2014.
Notice of Allowance dated Dec. 1, 2016, for U.S. Appl. No. 14/977,361, filed Dec. 21, 2015.

Primary Examiner — Deborah D Carr
(74) Attorney, Agent, or Firm — Jeremy Forest

(57) ABSTRACT

Provided herein are polyol estolide compounds. Polyol estolides may be prepared by contacting a polyol with an estolide compound. Also provided are compositions containing polyol estolides and methods of making the same.

15 Claims, No Drawings

POLYOL ESTOLIDES AND METHODS OF MAKING AND USING THE SAME

FIELD

The present disclosure relates to base oil stocks and lubricants and methods of making the same. The polyol estolides described herein may be suitable for use as biodegradable base oil stocks and lubricants, or lubricant additives.

BACKGROUND

A variety of commercial uses for fatty esters such as triglycerides have been described. When used as a lubricant, for example, fatty esters can provide a biodegradable alternative to petroleum-based lubricants. However, naturally-occurring fatty esters are typically deficient in one or more areas, including hydrolytic stability and/or oxidative stability.

SUMMARY

Described herein are estolide compounds, polyol estolide compounds and compositions, and methods of making the same. In certain embodiments, such compounds and/or compositions may be useful as a base oil, lubricant, or lubricant additive. In certain embodiments, the polyol estolides comprise at least one compound selected from Formula I:

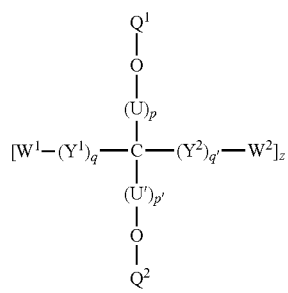

Formula I wherein
p is an integer selected from 0 to 10;
p' is an integer selected from 0 to 10;
z is an integer selected from 0 to 5;
q is, independently for each occurrence, an integer selected from 0 to 10;
q' is, independently for each occurrence, an integer selected from 0 to 10;
U is, independently for each occurrence, selected from —C($R^3$)$_2$—;
U' is, independently for each occurrence, selected from —C($R^4$)$_2$—;
$Y^1$ is, independently for each occurrence, selected from —C($R^5$)$_2$—, —$NR^7$—, —O—, —S—, —C(O)O—, and —O(O)C—;
$Y^2$ is, independently for each occurrence, selected from —C($R^6$)$_2$—, —$NR^7$—, —O—, —S—, —C(O)O—, and —O(O)C—;
$R^3$, $R^4$, $R^5$, $R^6$, and $R^7$ independently for each occurrence, are selected from hydrogen and optionally substituted alkyl that is saturated or unsaturated, and branched or unbranched;

$W^1$ is, independently for each occurrence, selected from hydrogen, optionally substituted alkyl that is saturated or unsaturated, and branched or unbranched, and —O-$Q^3$;
$W^2$ is, independently for each occurrence, selected from hydrogen, optionally substituted alkyl that is saturated or unsaturated, and branched or unbranched, and —O-$Q^4$; and
$Q_1$, $Q_2$, $Q_3$, and $Q_4$, independently for each occurrence, are selected from hydrogen and residues represented by Formula II:

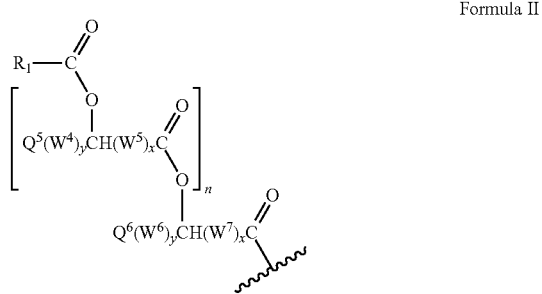

Formula II wherein
x is, independently for each occurrence, an integer selected from 0 to 20;
y is, independently for each occurrence, an integer selected from 0 to 20;
n is 0 or greater than 0;
$Q^5$ and $Q^6$, independently for each occurrence, are selected from hydrogen and —$CH_3$;
$R_1$ is, independently for each occurrence, selected from optionally substituted alkyl that is saturated or unsaturated, and branched or unbranched; and
$W^4$, $W^5$, $W^6$, and $W^7$, independently for each occurrence, are selected from —$CH_2$— and —CH=CH—,
wherein each fatty acid chain residue of said at least one compound is independently optionally substituted.

In certain embodiments, at least one of $Q_1$, $Q_2$, $Q_3$, and $Q_4$ is selected from residues of Formula II.

In certain embodiments, the at least one compound of Formula I is selected from compounds represented by Formula III:

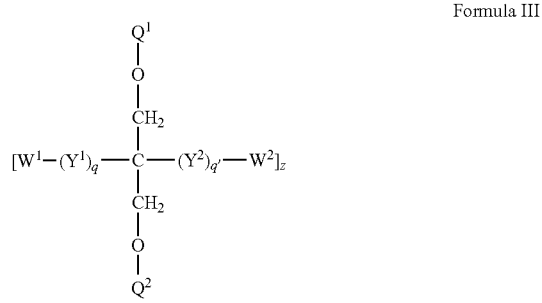

Formula III

In certain embodiments, the at least one compound of Formula I is selected from compounds represented by Formula IV:

Formula IV

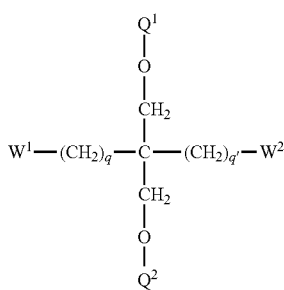

In certain embodiments, the estolides comprise at least one compound selected from Formula V:

Formula V

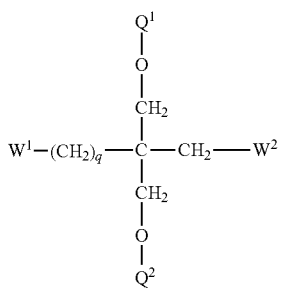

Also described herein, in certain embodiments is a method of preparing a polyol estolide compound, comprising providing at least one polyol and at least one estolide compound; and contacting the at least one polyol with the at least one estolide compound to provide the polyol estolide compound.

DETAILED DESCRIPTION

The estolide compounds and compositions described herein may exhibit superior properties when compared to other lubricant compositions. Exemplary compositions include, but are not limited to, coolants, fire-resistant and/or non-flammable fluids, dielectric fluids such as transformer fluids, greases, drilling fluids, crankcase oils, hydraulic fluids, passenger car motor oils, 2- and 4-stroke lubricants, metalworking fluids, food-grade lubricants, refrigerating fluids, compressor fluids, and plasticized compositions.

The use of lubricants and lubricating fluid compositions may result in the dispersion of such fluids, compounds, and/or compositions in the environment. Petroleum base oils used in common lubricant compositions, as well as additives, are typically non-biodegradable and can be toxic. The present disclosure provides for the preparation and use of compositions comprising partially or fully bio-degradable base oils, including base oils comprising one or more estolides.

In certain embodiments, the lubricants and/or compositions comprising one or more estolides are partially or fully biodegradable and thereby pose diminished risk to the environment. In certain embodiments, the lubricants and/or compositions meet guidelines set for by the Organization for Economic Cooperation and Development (OECD) for degradation and accumulation testing. The OECD has indicated that several tests may be used to determine the "ready biodegradability" of organic chemicals. Aerobic ready biodegradability by OECD 301D measures the mineralization of the test sample to $CO_2$ in closed aerobic microcosms that simulate an aerobic aquatic environment, with microorganisms seeded from a waste-water treatment plant. OECD 301D is considered representative of most aerobic environments that are likely to receive waste materials. Aerobic "ultimate biodegradability" can be determined by OECD 302D. Under OECD 302D, microorganisms are pre-acclimated to biodegradation of the test material during a pre-incubation period, then incubated in sealed vessels with relatively high concentrations of microorganisms and enriched mineral salts medium. OECD 302D ultimately determines whether the test materials are completely biodegradable, albeit under less stringent conditions than "ready biodegradability" assays.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH$_2$ is attached through the carbon atom.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

"Compounds" refers to compounds encompassed by structural Formula I-VI herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I-VI include, but are not limited to, optical isomers of compounds of Formula I-VI, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I-VI cover all asymmetric variants of the compounds described herein, including isomers, racemates, enantiomers, diastereomers, and other mixtures thereof. In addition, compounds of Formula I-VI include Z- and E-forms (e.g., cis- and trans-forms) of compounds with double bonds. The compounds of Formula I-VI may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Examples of substituents include, but are not limited to, —$R^{64}$, —$R^{60}$, —$O^-$, —OH, =O, —$OR^{60}$, —$SR^{60}$, —$S^-$, =S, —$NR^{60}R^{61}$, =$NR^{60}$, —CN, —$CF_3$, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O^-)$, —$OP(O)(R^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$, —$C(NR^{62})NR^{60}R^{61}$, —$S(O)_2, NR^{60}R^{61}$, —$NR^{63}S(O)_2R^{60}$, —$NR^{63}C(O)R^{60}$, and —$S(O)R^{60}$;

wherein each —$R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, —O-haloalkyl, -alkyl-$NH_2$, alkoxy, cycloalkyl, cycloalkylalkyl, heterocycloalkyl, heterocycloalkylalkyl, aryl, heteroaryl, arylalkyl, heteroarylalkyl, —$O^-$, —OH, =O, —O-alkyl, —O-aryl, —O-heteroarylalkyl, —O-cycloalkyl, —O-heterocycloalkyl, —SH, —$S^-$, =S, —S-alkyl, —S-aryl, —S-heteroarylalkyl, —S-cycloalkyl, —S-heterocycloalkyl, —$NH_2$, =NH, —CN, —$CF_3$, —OCN, —SCN, —NO, —$NO_2$, =$N_2$, —$N_3$, —$S(O)_2O^-$, —$S(O)_2$, —$S(O)_2OH$, —$OS(O_2)O^-$, —$SO_2$(alkyl), —$SO_2$(phenyl), —$SO_2$(haloalkyl), —$SO_2NH_2$, —$SO_2NH$(alkyl), —$SO_2NH$(phenyl), —$P(O)(O^-)_2$, —$P(O)(O$-alkyl$)(O^-)$, —$OP(O)(O$-alkyl$)(O$-alkyl$)$, —$CO_2H$, —C(O)O(alkyl), —CON(alkyl)(alkyl), —CONH(alkyl), —$CONH_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

The term "fatty acid" refers to any natural or synthetic carboxylic acid comprising an alkyl chain that may be saturated, monounsaturated, or polyunsaturated, and may have straight or branched chains. The fatty acid may also be substituted. "Fatty acid," as used herein, includes short chain alkyl carboxylic acid including, for example, acetic acid, propionic acid, etc.

All numerical ranges herein include all numerical values and ranges of all numerical values within the recited range of numerical values.

The present disclosure relates to polyol estolide compounds, compositions, and methods of making the same. In certain embodiments, the present disclosure relates to biosynthetic polyol estolides having one or more desirable physical properties, such as improved viscometrics, pour point, oxidative stability, hydrolytic stability, and/or viscosity index. In certain embodiments, the present disclosure relates to new methods of preparing estolide compounds exhibiting such properties.

In certain embodiments, the polyol estolides comprise at least one compound selected from Formula I:

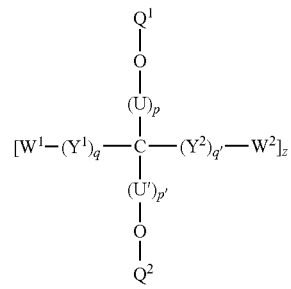

Formula I wherein p is an integer selected from 0 to 10;

p' is an integer selected from 0 to 10;

z is an integer selected from 0 to 5;

q is, independently for each occurrence, an integer selected from 0 to 10;

q' is, independently for each occurrence, an integer selected from 0 to 10;

U is, independently for each occurrence, selected from —$C(R^3)_2$—;

U' is, independently for each occurrence, selected from —$C(R^4)_2$—;

$Y^1$ is, independently for each occurrence, selected from —$C(R^5)_2$—, —$NR^7$—, —O—, —S—, —C(O)O—, and —O(O)C—;

$Y^2$ is, independently for each occurrence, selected from —$C(R^6)_2$—, —$NR^7$—, —O—, —S—, —C(O)O—, and —O(O)C—;

$R^3$, $R^4$, $R^5$, $R^6$, and $R^7$ independently for each occurrence, are selected from hydrogen and optionally substituted alkyl that is saturated or unsaturated, and branched or unbranched;

$W^1$ is, independently for each occurrence, selected from hydrogen, optionally substituted alkyl that is saturated or unsaturated, and branched or unbranched, and —O-$Q^3$;

$W^2$ is, independently for each occurrence, selected from hydrogen, optionally substituted alkyl that is saturated or unsaturated, and branched or unbranched, and —O-$Q^4$; and $Q_1$, $Q_2$, $Q_3$, and $Q_4$, independently for each occurrence, are selected from residues represented by Formula II:

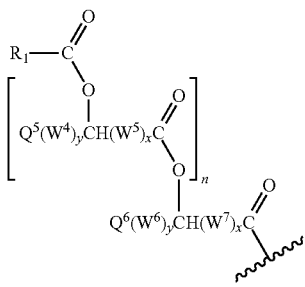

Formula II wherein x is, independently for each occurrence, an integer selected from 0 to 20;

y is, independently for each occurrence, an integer selected from 0 to 20;

n is 0 or greater than 0;

$Q^5$ and $Q^6$, independently for each occurrence, are selected from hydrogen and —$CH_3$;

$R_1$ is, independently for each occurrence, selected from optionally substituted alkyl that is saturated or unsaturated, and branched or unbranched; and $W^4$, $W^5$, $W^6$, and $W^7$, independently for each occurrence, are selected from —$CH_2$— and —CH=CH—, wherein each fatty acid chain residue of said at least one compound is independently optionally substituted.

In certain embodiments, at least one of $Q_1$, $Q_2$, $Q_3$, and $Q_4$ is selected from residues of Formula II.

In certain embodiments, the at least one compound of Formula I is selected from compounds represented by Formula III:

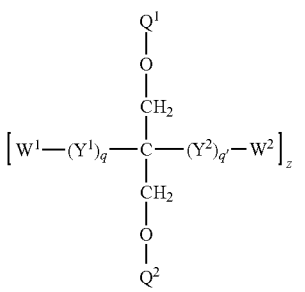

Formula III

In certain embodiments, the at least one compound of Formula I is selected from compounds represented by Formula IV:

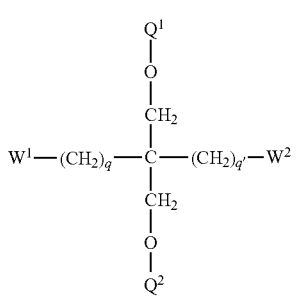

Formula IV

In certain embodiments, the estolides comprise at least one compound selected from Formula V:

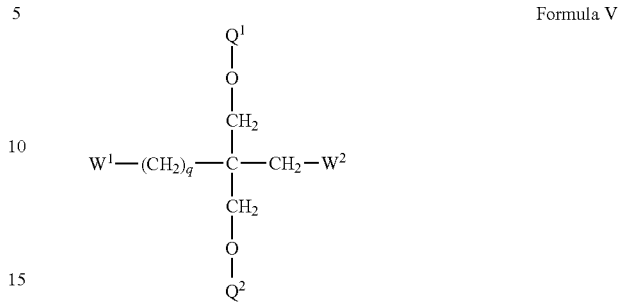

Formula V

Also described herein, in certain embodiments is a method of preparing a polyol estolide compound, comprising providing at least one polyol and at least one estolide compound; and contacting the at least one polyol with the at least one estolide compound to provide the polyol estolide compound.

In certain embodiments, the composition comprises at least one estolide according to Formulas I-VI, wherein $R_1$ is hydrogen.

The terms "chain" or "fatty acid chain" or "fatty acid chain residue," as used with respect to the polyol estolide compounds of Formulas I-VI, refer to one or more of the fatty acid residues comprising substituents of Formulas II and VI, e.g., the structures represented by $Q^5(W^4)_yCH(W)_xC(O)O$— and $Q^6(W^6)_yCH(W^7)_xC(O)O$— in Formula II, and the structures represented by $CH_3(CH_2)_yCH(CH_2)_xC(O)O$— in Formula VI.

The residues $R_1C(O)O$— in Formulas II and VI at the top of each Formula shown is an example of what may be referred to as "caps" or "capping materials," as it "caps" the top of the estolide substituent. In certain embodiments, the "caps" or "capping groups" are fatty acids. Similarly, the capping group may be an organic acid residue of general formula —OC(O)-alkyl, i.e., a carboxylic acid with an substituted or unsubstituted, saturated or unsaturated, and/or branched or unbranched alkyl as defined herein. In certain embodiments, the capping groups, regardless of size, are substituted or unsubstituted, saturated or unsaturated, and/or branched or unbranched. The caps or capping materials may also be referred to as the primary or alpha (α) chains. In certain embodiments the estolides are described as "poly-capped," wherein the compounds comprise two or more primary chains.

Depending on the manner in which the estolide is synthesized, the caps may be the only residues in the resulting estolide that are unsaturated. In certain embodiments, it may be desirable to use saturated organic or fatty-acid caps to increase the overall saturation of the estolide and/or to increase the resulting estolide's stability. For example, in certain embodiments, it may be desirable to provide a saturated capped estolide by epoxidizing, sulfurizing, and/or hydrogenating an unsaturated cap using any suitable methods available to those of ordinary skill in the art. Epoxidizing, sulfurizing, and/or hydrogenating may be used with various sources of the fatty-acid feedstock, which may include mono- and/or polyunsaturated fatty acids.

Without being bound to any particular theory, in certain embodiments, epoxidizing the estolide residue of the polyol estolide may help to improve the solubility and/or miscibility of the compound in certain compositions, such as those containing polymeric materials. Alternatively, in certain embodiments, epoxidizing an estolide substituent may provide for an intermediate compound, wherein the epoxide residue may be opened by reacting it with one or more compounds or compositions. For example, in certain embodiments, the epoxide residue of an epoxy estolide substituent is opened to provide a mono-hydroxy estolide or a dihydroxy estolide. In certain embodiments, exposing an epoxy estolide residue to aqueous acid conditions will provide a dihydroxy estolide. In certain embodiments, reacting an epoxy estolide residue with an alcohol (e.g., fatty alcohol) under acidic conditions will provide a mono-hydroxy estolide substituted with an alkoxy group. In certain embodiments, the epoxide residue may be opened by reacting the epoxy estolide residue with a carboxylic acid (e.g., fatty acid) to provide the mono-hydroxy estolide. In certain embodiments, polyol estolides having free hydroxy groups may be acylated to provide poly-capped estolides.

In certain embodiments, it may be desirable to provide a method of preparing a saturated capped estolide residue by hydrogenating one or more of the unsaturated caps using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide residues may help to improve the overall stability of the polyol estolide molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

The structures $Q^6(W^6)_y CH(W^7)_x C(O)O$— of Formula II and $CH_3(CH_2)_y CH(CH_2)_x C(O)O$— of Formula VI represent the "base" or "base chain residue" of the estolide substituent. Depending on the manner in which the polyol estolide is synthesized, the base organic acid or fatty acid residue may initially remain in its free-acid form during the early stages of the compounds synthesis (i.e., free-acid estolide formation). Subsequently, the free-acid estolide may be condensed with one or more hydroxy residues of a polyol to form the polyol estolide. Alternatively, in certain embodiments, the polyol estolide may be prepared by condensing a free fatty acid (e.g., hydroxylated or unsaturated) with the free hydroxy group(s) of a polyol to form a polyol ester. Subsequently, additional fatty acids may be added to the fatty acid residues of the polyol ester via, e.g., sites of hydroxylation or unsaturation, to provide a polyol estolide. The base or base chain residue may also be referred to as tertiary or gamma (γ) chains.

The structures $Q^5(W^4)_y CH(W^5)_x C(O)O$— of Formula II and $CH_3(CH_2)_y CH(CH_2)_x C(O)O$— of Formula VI represent linking residues that link the capping material and the base fatty-acid residue of the estolide substituent. Depending on the manner in which the polyol estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In certain embodiments, the formation of the carbocation will result in a mixture of estolide isomers, wherein the bond between two fatty acid residues takes place at one of two available carbon linking sites (e.g., estolide linkage at primarily the (18:1 n-9) and (18:1 n-10) positions of oleic acid residues). In certain embodiments, polyunsaturated fatty acids may provide multiple carbocations for the addition of two or more fatty acids to the polyunsaturated residue to provide, for example, poly-capped estolide substituents. In some embodiments, it may be desirable to have a linking fatty acid that is mono-unsaturated so that when the fatty acids link together, all of the sites of unsaturation are eliminated. The linking residue (s) may also be referred to as secondary or beta (β) chains.

As noted above, in certain embodiments, suitable unsaturated fatty acids for preparing the polyol estolides may include any mono- or polyunsaturated fatty acid. For example, monounsaturated fatty acids, along with a suitable catalyst, will form a single carbocation of the addition of a second fatty acid, whereby a single link between two fatty acids (e.g., between β-chain and γ-chain, and β-chain and α-chain) is formed. Suitable monounsaturated fatty acids may include, but are not limited to, palmitoleic (16:1), vaccenic (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21: 5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5). In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

Because polyunsaturated fatty acids have more than one site of unsaturation, the resulting polyol estolide may comprise unsaturated chains and/or chains substituted with two or more fatty acids. For example, preparing a polyol estolide from linoleic and/or linolenic acid can result in estolide substituents having two or more caps. In certain embodiments, linoleic and/or linolenic acid is reacted with an organic and/or fatty acid to provide an estolide substituent having two or more caps. In some embodiments, the organic and/or fatty acid cap comprises a $C_1$-$C_{40}$ alkyl residue. In some embodiments, the organic acid cap is acetic acid. In some embodiment, the fatty acid cap comprises a $C_7$-$C_{17}$ alkyl residue.

The process for preparing the estolide compounds described herein may include the use of any natural or synthetic fatty acid source. However, it may be desirable to source the fatty acids from a renewable biological feedstock. Suitable starting materials of biological origin may include plant fats, plant oils, plant waxes, animal fats, animal oils, animal waxes, fish fats, fish oils, fish waxes, algal oils and mixtures thereof. Other potential fatty acid sources may include waste and recycled food-grade fats and oils, fats, oils, and waxes obtained by genetic engineering, fossil fuel based materials and other sources of the materials desired.

In certain embodiments, the estolide compounds described herein may be prepared from non-naturally occurring fatty acids derived from naturally occurring feedstocks. In certain embodiments, the estolides are prepared from synthetic fatty acid reactants derived from naturally occurring feedstocks such as vegetable oils. For example, the synthetic fatty acid reactants may be prepared by cleaving fragments from larger fatty acid residues occurring in natural oils such as triglycerides using, for example, a cross-metathesis catalyst and alpha-olefin(s). The resulting truncated fatty acid residue(s) may be liberated from the glycerine backbone using any suitable hydrolytic and/or transesterification processes known to those of skill in the art. An exemplary fatty acid reactant includes 9-dodecenoic acid, which may be prepared via the cross metathesis of an oleic acid residue with 1-butene. In certain embodiments, the estolide may be prepared from fatty acids having a terminal site of unsaturation (e.g., 9-decenoic acid), which may be prepared via the cross metathesis of an oleic acid residue with ethene.

In certain embodiments, the polyol estolide is prepared by reacting at least one polyol with at least one estolide compound, such as a free acid estolide compound. In certain embodiments, the at least one polyol estolide may be contacted with at least one estolide ester, such as an estolide methyl ester. Alternatively, in certain embodiments, the polyol estolide is prepared by contacting at least one polyol ester comprising one or more fatty acid residues having at least one reactive site. For example, in certain embodiments, one or more fatty acid residues of the polyol ester will comprise a reactive site that allows for the formation of a polyol estolide when contacted with one or more free fatty acids. Exemplary methods of preparing the polyol estolides are set forth in Schemes 1 and 2.

In certain embodiments, the estolide comprises fatty-acid chains of varying lengths. In some embodiments, z, p, p', q and q' are independently an integer selected from 0 to 15, 0 to 12, 0 to 10, 0 to 8, 0 to 6, 0 to 4, and 0 to 2. For example, in some embodiments, z is an integer selected from 0 to 5 or 0 to 3, such as 1, 2, or 3. In some embodiments, z is 0. In certain embodiments, z is 1. In some embodiments, p and p' are independently an integer selected from 0 to 5, such as 1 to 5, 0 to 3, or 1 to 3. In some embodiments, p is 1. In certain embodiments, p' is 1. In some embodiments, q and q' are independently for each occurrence an integer selected from 0 to 15, 0 to 10, 0 to 6, 0 to 5, 0 to 3, and 0 to 2. In some embodiments, q and q', independently for each occurrence, are an integer selected from 1 and 2. In some embodiments, z, p, p', q and q', independently for each occurrence, are selected from 0, 1, 2, 3, 4, 5, 6, 6, 8, 9, 10, 11, 12, 13, 14 and 15.

In some embodiments, $W^1$ is, independently for each occurrence, selected from hydrogen, optionally substituted alkyl that is saturated or unsaturated, and branched or unbranched, and —O-$Q^3$. In certain embodiments, $W^1$ is hydrogen. In certain embodiments, $W^2$ is, independently for each occurrence, selected from hydrogen, optionally substituted alkyl that is saturated or unsaturated, and branched or unbranched, and —O-$Q^4$. In certain embodiments, $W^1$ and $W^2$, independently for each occurrence, are selected from hydrogen and optionally substituted alkyl that is saturated or unsaturated, and branched or unbranched. In certain embodiments, $W^1$ and $W^2$, independently for each occurrence, are selected from —O-$Q^3$ and —O-$Q^4$, respectively. In certain embodiments, $W^1$ is, independently for each occurrence, selected from optionally substituted $C_1$ to $C_{20}$ alkyl that is saturated or unsaturated, and branched or unbranched. In certain embodiments, $W^2$ is, independently for each occurrence, selected from optionally substituted $C_1$ to $C_{20}$ alkyl that is saturated or unsaturated, and branched or unbranched.

In certain embodiments, $Q_1$, $Q_2$, $Q_3$, and $Q_4$, independently for each occurrence, are selected from residues represented by Formula II:

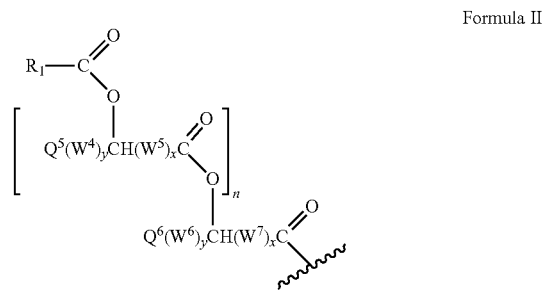

Formula II

In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y, for one or more of the fatty acid chain residues, is 15. In some embodiments, x+y is, independently for each chain, an integer selected from 6, 7, 8, 9, 10, 11, 12, 13, 14, 15, 16, 17, 18, 19, 20, 21, 22, 23, and 24.

In some embodiments, the estolide compound may comprise any number of fatty acid residues to form one or more "n-mer" estolide residues. The polyol estolide compounds of Formulas I-VI may comprise one or more estolide residues in their dimer (n=0), trimer (n=1), tetramer (n=2), pentamer (n=3), hexamer (n=4), heptamer (n=5), octamer (n=6), nonamer (n=7), or decamer (n=8) form. For example, polyol estolide compounds of Formula V may comprise four estolide residues of Formula II when $W^1$ and $W^2$ are selected from —O-$Q_3$ and —O-$Q_4$, respectively.

In some embodiments, n is, independently for each occurrence, an integer selected from 0 to 20, 0 to 18, 0 to 16, 0 to 14, 0 to 12, 0 to 10, 0 to 8, or 0 to 6. In some embodiments, n is, independently for each occurrence, an integer selected from 0 to 4. In some embodiments, n is 0 for each occurrence. In some embodiments, n is, independently for each occurrence, an integer that is equal to or greater than 1. In some embodiments, n is, independently for each occurrence, an integer selected from 1 to 12, 1 to 8, or 1 to 4. In some embodiments, n is, independently for each occurrence, an integer selected from 0, 1, 2, 3, 4, 5, 6, 7, 8, 9, 10, 11, and 12.

In certain embodiments, $W^4$, $W^5$, $W^6$, and $W^7$, independently for each occurrence, are selected from —$CH_2$— and —CH=CH—. In certain embodiments, $W^4$, $W^5$, $W^6$, and $W^7$ for each occurrence are —$CH_2$—.

In certain embodiments, $Q^5$ and $Q^6$, independently for each occurrence, are selected from hydrogen and —$CH_3$. For example, in certain embodiments, estolides of Formulas I-VI are prepared from terminally-unsaturated fatty acids such as 9-decenoic acid and/or 10-undecenoic acid. In certain embodiments, oligomerizing terminally-unsaturated fatty acids such as 9-decenoic acid and/or 10-undecenoic acid will provide free acid estolides comprising a first fatty acid residue linked to the terminal carbon or penultimate carbon of a second fatty acid residue. In certain embodiments, polyol estolides prepared from terminally-unsaturated fatty acids will exhibit certain desirable properties, including viscosity and low-temperature properties. Without being bound to any particular theory, it is believed that the terminal unsaturation allows for the production of larger oligomers that have shorter hydrocarbon chain residues when compared to certain naturally-occurring fatty acids (e.g., $C_{18}$ fatty acids). The a higher degree of oligomerization, coupled the lower crystallization temperature that can be associated with shorter fatty acid residues, may provide polyol estolides that have desirable viscomertrics (e.g., higher viscosity) and low pour points (e.g. less than −30° C. or even −40° C.). Thus, in certain embodiments, for compounds according to Formulas I-VI, y is 0 and $Q^5$ and $Q^6$ are independently selected from hydrogen and —$CH_3$ for each occurrence. In certain embodiments, n is 0, y is 0, and $Q^6$ is selected from hydrogen and —$CH_3$. Exemplary procedures for preparing estolide compounds from terminally-unsaturated fatty acids can be found in U.S. patent application Ser. No. 13/707,480, filed Dec. 6, 2012, which is incorporated herein by reference in its entirety for all purposes.

In certain embodiments, $R^3$, $R^4$, $R^5$, $R^6$, and $R^7$, independently for each occurrence, are selected from hydrogen and an optionally substituted alkyl that is saturated or unsaturated, and branched or unbranched. In certain embodiments, $R^3$, $R^4$, $R^5$, $R^6$, and $R^7$ are hydrogen for each occurrence. In certain embodiments, $R^3$, $R^4$, $R^5$, $R^6$, and $R^7$ are independently selected from hydrogen and $C_1$-$C_{20}$ alkyl. In certain embodiments, $R^3$, $R^4$, $R^5$, $R^6$, and $R^7$ are independently selected from hydrogen and $C_1$-$C_{10}$ alkyl.

In some embodiments, $R_1$, independently for each occurrence, is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{17}$ alkyl. In some embodiments, the alkyl group is selected from $C_7$ to $C_{17}$ alkyl, $C_3$ to $C_{13}$ alkyl, or $C_5$ to $C_{11}$ alkyl. In some embodiments, each $R_1$ is independently selected from $C_1$ alkyl, $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl, $C_{20}$ alkyl, $C_{21}$ alkyl, $C_{22}$ alkyl, $C_{23}$ alkyl, and $C_{24}$ alkyl. In some embodiments, each $R_1$ is methyl. In some embodiments, $R_1$ is independently selected from $C_{13}$ to $C_{17}$ alkyl, such as from $C_{13}$ alkyl, $C_{15}$ alkyl, and $C_{17}$ alkyl.

It may be possible to manipulate one or more of the estolides' properties by altering the length of $R_1$ and/or its degree of saturation. However, the level of substitution on $R_1$ may also be altered to change or even improve the estolides' properties. Without being bound to any particular theory, it is believed that the presence of polar substituents on $R_1$, such as one or more hydroxy groups, may increase the viscosity of the estolide, while adversely increasing pour point. Accordingly, in some embodiments, $R_1$ will be unsubstituted or optionally substituted with a group that is not hydroxyl.

In some embodiments, the compounds described herein may comprise a mixture of polyol estolide compounds having estolide residues of varying size and complexity. It is possible to characterize the chemical makeup of a polyol estolide, a mixture of polyol estolides, or a composition comprising polyol estolides by using the compound's, mixture's, or composition's, measured estolide number (EN). The EN of a polyol estolide represents the average number of fatty acids added to base fatty acids comprising said polyol estolide. The EN also represents the average number of estolide linkages per molecule. For example, with respect to the estolide residue of Formula II:

EN=n+1 wherein n is the number of secondary (β) fatty acids. Accordingly, a single estolide residue will have an EN that is a whole number, for example for dimers, trimers, and tetramers:

dimer EN=1 trimer EN=2 tetramer EN=3

However, a polyol estolide compound, or mixture of polyol estolides, may have an EN that is a whole number or a fraction of a whole number. For example, a polyol estolide compound having a 1:1 ratio of dimer and trimer would have an EN of 1.5, while a polyol estolide having a 1:1 molar ratio of tetramer and trimer would have an EN of 2.5. Similarly, a composition comprising the following polyol estolides would have an EN of 1.5, representing the average number of linkages amongst polyol estolide Compounds A and B in the composition:

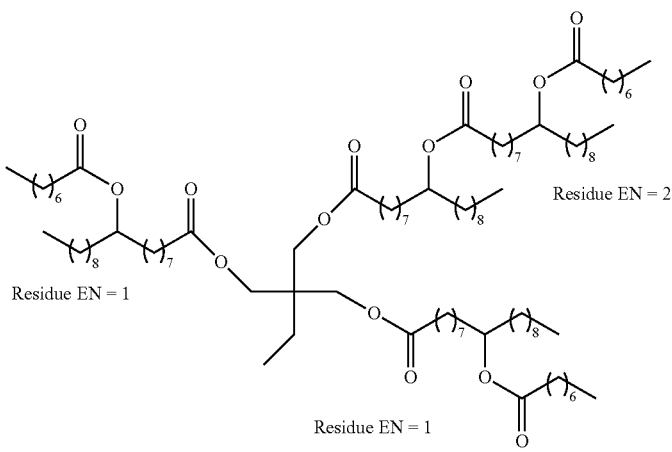

"Compound A" EN = 1.33

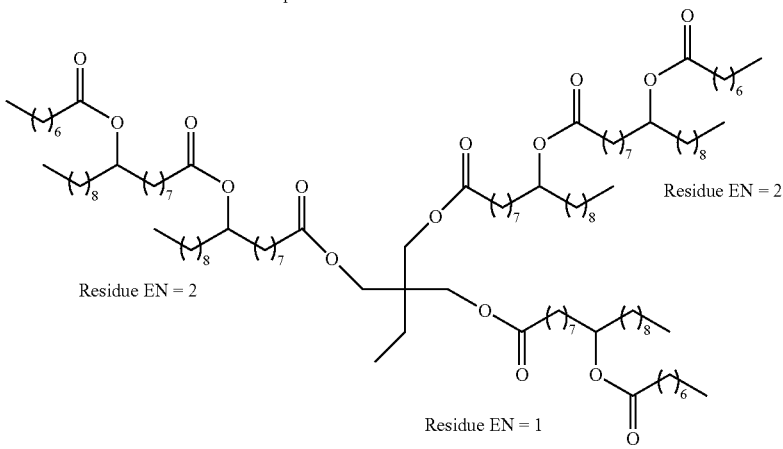

"Compound B" EN = 1.67

In some embodiments, the compositions may comprise a mixture of two or more polyol estolides having an EN that is an integer or fraction of an integer that is greater than or equal to 1. In some embodiments, the EN may be an integer or fraction of an integer selected from about 1.0 to about 5.0. In some embodiments, the EN is an integer or fraction of an integer selected from 1.2 to about 4.5. In some embodiments, the estolide compounds described herein will be in there trimer form or larger, wherein the EN is greater than or equal to 2. Thus, in some embodiments, the EN is selected from an integer or fraction of an integer that is from about 2.0 to about 3.0, or from about 2.2 to about 2.8. In certain embodiments, the EN is selected from an integer or fraction of an integer that is less than or equal to 2, or less than or equal to 1.5. In certain embodiments, the EN is selected from an integer or fraction of an integer that is from about 1 to about 1.5, such as about 1.0 to about 1.3. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0.

Without being bound to any particular theory, in certain embodiments, altering the EN produces estolides having the desired viscometric properties while substantially retaining or even reducing pour point. For example, in some embodiments polyol estolides exhibit a decreased pour point upon increasing the EN value. Accordingly, in certain embodiments, a method is provided for retaining or decreasing the pour point of polyol estolide oil by increasing the EN of the oil, or a method is provided for retaining or decreasing the pour point of a composition comprising polyol estolide oil by increasing the EN of the base oil. In some embodiments, the method comprises: selecting an polyol estolide base oil having an initial EN and an initial pour point; and removing at least a portion of the polyol estolide base oil, said portion exhibiting an EN that is less than the initial EN of the polyol estolide, wherein the resulting polyol estolide base oil exhibits an EN that is greater than the initial EN of the base oil, and a pour point that is equal to or lower than the initial pour point of the base oil. In some embodiments, the selected polyol estolide base oil is prepared by a process that includes oligomerizing at least one first unsaturated fatty acid with at least one second unsaturated fatty acid and/or saturated fatty acid. In some embodiments, the removing at least a portion of the polyol estolide base oil is accomplished by distillation, chromatography, membrane separation, phase separation, affinity separation, or combinations thereof. In some embodiments, the distillation takes place at a temperature and/or pressure that is suitable to separate the polyol estolide base oil into different "cuts" that individually exhibit different EN values. In some embodiments, this may be accomplished by subjecting the base oil to a temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

Typically, base stocks and lubricant compositions exhibit certain lubricity, viscosity, and/or pour point characteristics. For example, in certain embodiments, suitable kinematic viscosity characteristics of the base oil may range from about 10 cSt to about 1000 cSt at 40° C., and/or about 2 cSt to about 80 cSt at 100° C. In some embodiments, the polyol estolide base stocks may exhibit kinematic viscosities within a range from about 200 cSt to about 900 cSt at 40° C., and/or about 20 cSt to about 80 cSt at 100° C.

In some embodiments, polyol estolide compounds and compositions may exhibit kinematic viscosities of at least 200 cSt at 40° C., or at least 225 cSt at 40° C., and/or at least 20 cSt at 100° C. or at least 25 cSt at 100° C. In some embodiments, polyol estolide compounds and compositions may exhibit kinematic viscosities of at least 250 cSt at 40° C. or at least 300 cSt at 40° C., and/or at least 30 cSt at 100° C. or at least 35 cSt at 100° C. In some embodiments, polyol estolide compounds and compositions may exhibit kinematic viscosities of at least 350 cSt at 40° C. or at least 400 cSt at 40° C., and/or at least 40 cSt at 100° C. or at least 45 cSt at 100° C. In some embodiments, polyol estolide compounds and compositions may exhibit kinematic viscosities of at least 450 cSt at 40° C. or at least 525 cSt at 40° C., and/or at least 50 cSt at 100° C. or at least 55 cSt at 100° C. In some embodiments, polyol estolide compounds and compositions may exhibit kinematic viscosities of at least 600 cSt at 40° C. or at least 720 cSt at 40° C., and/or at least 60 cSt at 100° C. or at least 65 cSt at 100° C. In some embodiments, polyol estolide compounds and compositions may exhibit kinematic viscosities of at least 800 cSt at 40° C. or at least 850 cSt at 40° C., and/or at least 70 cSt at 100° C. or at least 75 cSt at 100° C.

In certain embodiments, the polyol estolide compounds and compositions may exhibit kinematic viscosities of about 200 cSt at 40° C. to about 225 cSt at 40° C., and/or about 20 cSt at 100° C. to about 25 cSt at 100° C. In some embodiments, polyol estolide compounds and compositions may exhibit kinematic viscosities of about 250 cSt at 40° C. to about 300 cSt at 40° C., and/or about 30 cSt at 100° C. to about 35 cSt at 100° C. In some embodiments, polyol estolide compounds and compositions may exhibit kinematic viscosities of about 350 cSt at 40° C. to about 400 cSt at 40° C., and/or about 40 cSt at 100° C. to about 45 cSt at 100° C. In some embodiments, polyol estolide compounds and compositions may exhibit kinematic viscosities of about 450 cSt at 40° C. to about 525 cSt at 40° C., and/or about 50 cSt at 100° C. to about 55 cSt at 100° C. In some embodiments, polyol estolide compounds and compositions may exhibit kinematic viscosities of about 600 cSt at 40° C. to about 720 cSt at 40° C., and/or about 60 cSt at 100° C. to about 65 cSt at 100° C. In some embodiments, polyol estolide compounds and compositions may exhibit kinematic viscosities of about 800 cSt at 40° C. to about 850 cSt at 40° C., and/or about 70 cSt at 100° C. to about 75 cSt at 100° C.

In certain embodiments, polyol estolides may exhibit desirable low-temperature pour point properties. In some embodiments, polyol estolide compounds and compositions may exhibit a pour point lower than about −25° C., about −35° C., −40° C., −50° C., −60° C., −70° C., or even −80° C. In some embodiments, polyol estolides have a pour point of about −25° C. to about −45° C. In some embodiments, the pour point falls within a range of about −30° C. to about −40° C. In some embodiments, the pour point falls within the range of about −40° C. to about −50° C., or about −50° C. to about −60° C. In some embodiments, the pour point falls within the range of about −60° C. to about −70° C., or about −70° C. to about −80° C. In some embodiments, the pour point falls within the range of about −80° C. to about −85° C., or about −85° C. to about −90° C. In some embodiments, the pour point falls within the range of about −90° C. to about −100° C.

In addition, in certain embodiments, polyol estolides may exhibit decreased Iodine Values (IV) when compared to polyol estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of polyol estolides in an effort to increase the oil's oxidative stability, while also decreasing harmful deposits and the corrosiveness of the oil.

In some embodiments, polyol estolides described have an IV of less than about 40 cg/g or less than about 35 cg/g. In some embodiments, polyol estolides will have an IV of less than about 30 cg/g, less than about 25 cg/g, less than about 20 cg/g, less than about 15 cg/g, less than about 10 cg/g, or less than about 5 cg/g. The IV of a polyol estolide may be reduced by decreasing the estolide's degree of unsaturation. In certain embodiments, this may be accomplished by, for example, increasing the amount of saturated capping materials relative to unsaturated capping materials when synthesizing the estolides. Alternatively, in certain embodiments, IV may be reduced by hydrogenating polyol estolides having unsaturated caps.

In certain embodiments, methods of preparing a polyol estolide compound are described. In certain embodiments, the method comprises: providing at least one polyol and at least one estolide compound; and contacting the at least one polyol with the at least one estolide compound to provide the polyol estolide compound. In certain embodiments, the at least one polyol is contacted with at least one free-acid estolide compound. Exemplary polyols include, but are not limited to, 1,2- and 1,3-propanediol, diethylene glycol, dipropylene glycol, 1,4-butanediol, 1,6-hexanediol, glycerol, pentaerythritol, sorbitol, sucrose, neopentylglycol; 1,2-propylene glycol; trimethylolethane; trimethylolpropane; 1,6-hexanediol; 2,5-hexanediol; 1,4-butanediol; 1,4-cyclohexane diol; ethylene glycol; diethylene glycol; methylene glycol; 9(1)-hydroxymethyloctadecanol, and 1,4-bishydroxymethylcyclohexane.

In certain embodiments, the at least one polyol is contacted with the at least one estolide compound in the presence of a catalyst. Suitable catalysts may include one or more Lewis acids and/or Bronsted acids, including, for example, AgOTf, Cu(OTf)$_2$, Fe(Otf)$_2$, Fe(Otf)$_3$, NaOTf, LiOTf, Yb(Otf)$_3$, Y(Otf)$_3$, Zn(Otf)$_2$, Ni(Otf)$_2$, Bi(Otf)$_3$, La(Otf)$_3$, Sc(Otf)$_3$, hydrochloric acid, nitric acid, sulfuric acid, methanesulfonic acid, phosphoric acid, perchloric acid, triflic acid, and p-TsOH. In certain embodiments, the catalyst may comprise a strong Lewis acid such as BF$_3$ etherate.

In certain embodiments, the reaction is conducted in the presence of dielectric heating, such as microwave radiation.

In some embodiments, the catalyst may comprise a Lewis acid catalyst, such as at least one metal compound selected from one or more of titanium compounds, tin compounds, zirconium compounds, and hafnium compounds. In certain embodiments, the catalyst is at least one titanium compound selected from $TiCl_4$ and $Ti(OCH_2CH_2CH_2CH_3)_4$ (titanium (IV) butoxide). In certain embodiments, the catalyst is at least one tin compound selected from $Sn(O_2CCO_2)$ (tin (II) oxalate), SnO, and $SnCl_2$. In some embodiments, the catalyst is at least one zirconium compound selected from $ZrCl_4$, $ZrOCl_2$, $ZrO(NO_3)_2$, $ZrO(SO_4)$, and $ZrO(CH_3COO)_2$. In certain embodiments, the catalyst is at least one hafnium compound selected from $HfCl_2$ and $HfOCl_2$. Unless stated otherwise, all metal compounds and catalysts discussed herein should be understood to include their hydrate and solvate forms. For example, in certain embodiments, the catalyst may be selected from $ZrOCl_2 \cdot 8H_2O$ and $ZrOCl_2 \cdot 2THF$, or $HfOCl_2 \cdot 2THF$ and $HfOCl_2 \cdot 8H_2O$.

In certain embodiments, contacting the polyl with an estolide compound will result in partial esterification of the polyl. Accordingly, in certain embodiments, the resulting polyl estolide composition will exhibit a hydroxyl value of greater than 0 mg KOH/g. In certain embodiments, the composition exhibits a hydroxyl value less than or equal to 1 mg KOH/g. In certain embodiments, the composition exhibits a hydroxyl value less than or equal to 5 mg KOH/g. In certain embodiments, the composition exhibits a hydroxyl value less than or equal to 20 mg KOH/g, such as 5 to 10 mg KOH/g or 10 to 15 mg KOH/g. In certain embodiments, the composition exhibits a hydroxyl value greater than or equal to 20 mg KOH/g, such as 20 to 30 mg KOH/g or 30 to 40 mg KOH/g. In certain embodiments, the composition exhibits a hydroxyl value greater than or equal to 40 mg KOH/g, such as 40 to 50 mg KOH/g or 50 to 60 mg KOH/g. In certain embodiments, polyol estolides exhibiting higher hydroxyl values (e.g., greater than 10 mg KOH/g or even greater than 20 mg KOH/g) exhibit higher thermal and/or oxidative stability when measured using pressure differential scanning calorimetry (PDSC).

The present disclosure further relates to methods of making polyol estolides according to Formulas I-VI. By way of example, the reaction of a polyol with a free-acid estolide is illustrated and discussed below.

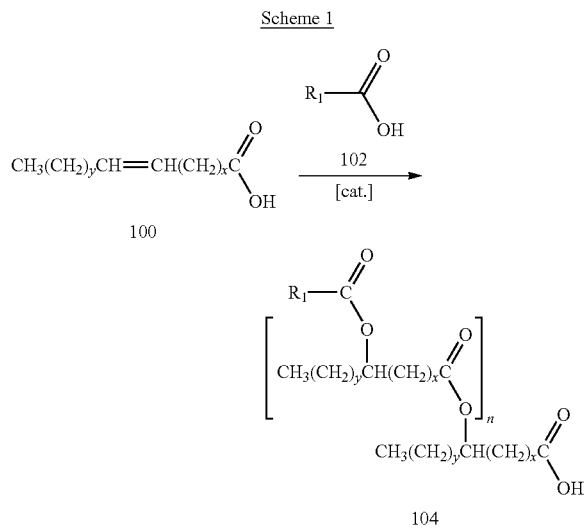

Scheme 1

In Scheme 1, wherein x is, independently for each occurrence, an integer selected from 0 to 20, y is, independently for each occurrence, an integer selected from 0 to 20, n is an integer greater than or equal to 0, and $R_1$ is an optionally substituted alkyl that is saturated or unsaturated, and branched or unbranched, unsaturated fatty acid 100 may be combined with compound 102 and a catalyst to form free acid estolide 104. In certain embodiments, compound 102 is not included, and unsaturated fatty acid 100 may be exposed alone to catalytic conditions to form free acid estolide 104, wherein $R_1$ would represent an unsaturated alkyl group. In certain embodiments, if compound 102 is included in the reaction, $R_1$ may represent one or more optionally substituted alkyl residues that are saturated or unsaturated and branched or unbranched. Any suitable proton source may be implemented to catalyze the formation of free acid estolide 104, including but not limited to homogenous acids and/or strong acids like hydrochloric acid, sulfuric acid, phosphoric acid, perchloric acid, nitric acid, triflic acid, and the like. Other suitable catalysts may include dielectric heating (e.g., microwave radiation) and/or Lewis acid catalysts (e.g., iron triflate).

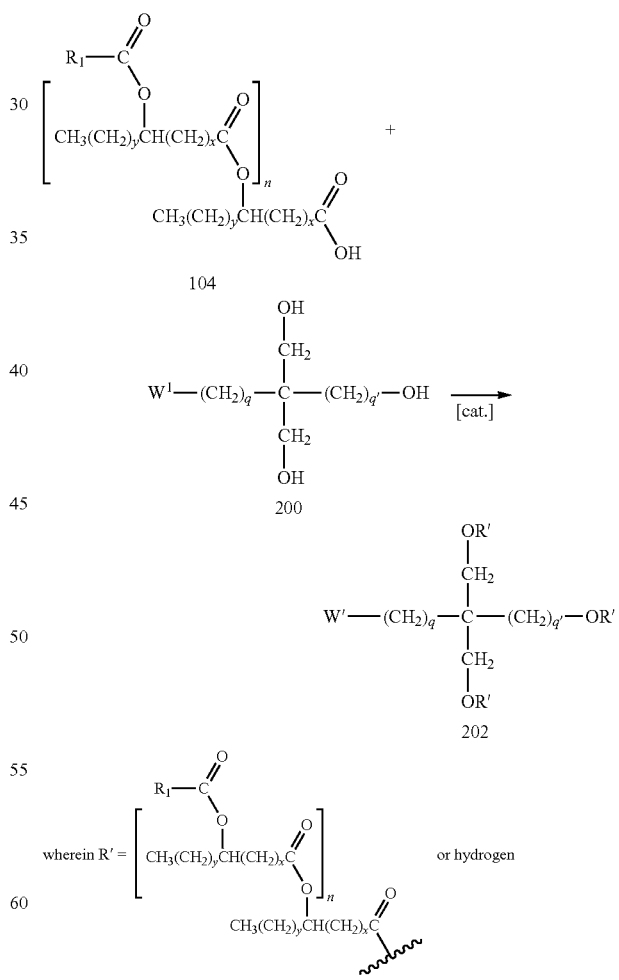

Scheme 2

In Scheme 2, wherein x is, independently for each occurrence, an integer selected from 0 to 20, y is, independently for each occurrence, an integer selected from 0 to 20, n is an integer greater than or equal to 0, $R_1$ is an optionally substituted alkyl that is saturated or unsaturated, and branched or unbranched, q and q' are, independently for each occurrence, an integer selected from 0 to 10, and $W^1$ is selected from hydrogen and —OH, free acid estolide 104 and polyol 200 are combined under catalytic conditions to form polyol estolide 202, wherein W' is hydrogen or —OR'. In certain embodiments, polyol 200 undergoes partial esterification with free acid estolide 104, such that one or more of R' are hydrogen. Any suitable proton source may be implemented to catalyze the formation of free acid estolide 200, including but not limited to homogenous acids and/or strong acids like hydrochloric acid, sulfuric acid, phosphoric acid, perchloric acid, nitric acid, triflic acid, and the like. Other suitable catalysts may include dielectric heating (e.g., microwave radiation) and/or Lewis acid catalysts (e.g., tin compounds such as stannous chloride).

In certain embodiments, polyol estolide compounds may meet or exceed one or more of the specifications for certain end-use applications, without the need for conventional additives. For example, in certain instances, high-viscosity lubricants, such as those exhibiting a kinematic viscosity of greater than about 100 cSt at 40° C., or even greater than about 200 cSt at 40° C., may be desirable for particular applications such as gearbox or wind turbine lubricants. Prior-known lubricants with such properties typically also demonstrate an increase in pour point as viscosity increases, such that prior lubricants may not be suitable for such applications in colder environments. However, in certain embodiments, the counterintuitive properties of certain compounds described herein (e.g., increased EN provides estolides with higher viscosities while retaining, or even decreasing, the oil's pour point) may make higher-viscosity estolides particularly suitable for such specialized applications.

Similarly, the use of prior-known lubricants in colder environments may generally result in an unwanted increase in a lubricant's viscosity. Thus, depending on the application, it may be desirable to use lower-viscosity oils at lower temperatures. In certain circumstances, low-viscosity oils may include those exhibiting a viscosity of lower than about 50 cSt at 40° C., or even about 40 cSt at 40° C. Accordingly, in certain embodiments, the low-viscosity estolides described herein may provide end users with a suitable alternative to high-viscosity lubricants for operation at lower temperatures.

In some embodiments, it may be desirable to prepare lubricant compositions comprising a polyol estolide base stock. For example, in certain embodiments, the polyol estolides described herein may be blended with one or more additives selected from polyalphaolefins, synthetic esters, polyalkylene glycols, mineral oils (Groups I, II, and III), pour point depressants, viscosity modifiers, anti-corrosives, antiwear agents, detergents, dispersants, colorants, antifoaming agents, and demulsifiers. In addition, or in the alternative, in certain embodiments, the polyol estolides described herein may be co-blended with one or more synthetic or petroleum-based oils to achieve the desired viscosity and/or pour point profiles. In certain embodiments, the estolides described herein also mix well with gasoline, so that they may be useful as fuel components or additives.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance: NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1H$ NMR by a peak at about 4.84 ppm.

Estolide Number (EN): The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV): The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than polyol estolides as set forth in Formula I-VI, the polyol estolides can be separated from other unsaturated compounds present in the composition prior to measuring the iodine value of the constituent estolides. For example, if a composition includes unsaturated fatty acids or triglycerides comprising unsaturated fatty acids, these can be separated from the polyol estolides present in the composition prior to measuring the iodine value for the one or more estolides.

Acid Value: The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC): GC analysis was performed to evaluate the estolide number (EN) and iodine value (IV) of the polyol estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC: To perform these analyses, the fatty acid components of an polyol estolide sample were reacted with MeOH to form fatty acid methyl esters by a method that left behind a hydroxy group at sites where estolide links were once present. Standards of fatty acid methyl esters were first analyzed to establish elution times.

Sample Preparation: To prepare the samples, 10 mg of polyol estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation: The EN is measured as the percent hydroxy fatty acids divided by the percent non-hydroxy fatty acids. As an example, a dimer estolide residue would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation: The iodine value is estimated by the following equation based on ASTM Method D97 (ASTM International, Conshohocken, Pa.):

$$IV = \Sigma\ 100 \times \frac{A_f \times MW_I \times db}{MW_f}$$

$A_f$=fraction of fatty compound in the sample
$MW_I$=253.81, atomic weight of two iodine atoms added to a double bond
db=number of double bonds on the fatty compound
$MW_f$=molecular weight of the fatty compound The properties of exemplary polyol estolide compounds and compositions described herein are identified in the following examples and tables.

Other Measurements: Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat#244252) and heated to 60° C. in vacuo (10 torr abs) for 24 hrs while continuously being agitated. After 24 hours the vacuum was released. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (µ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1µ filter back into the reactor. The reactor was heated to 60° C. in vacuo (10 torr abs) until all ethanol and water ceased to distill from solution. The remaining material was then distilled using a Myers 15 Centrifugal Distillation still at 200° C. under an absolute pressure of approximately 12 microns (0.012 torr) to remove unreacted fatty acids and leaving behind free-acid estolides (Ex. 1).

Example 2

The acid catalyst reaction was conducted in a 50 gallon Pfaudler RT-Series glass-lined reactor. Oleic acid (50 Kg, OL 700, Twin Rivers) and whole cut coconut fatty acid (18.754 Kg, TRC 110, Twin Rivers) were added to the reactor with 70% perchloric acid (1145 mL, Aldrich Cat#244252) and heated to 60° C. in vacuo (10 torr abs) for 24 hrs while continuously being agitated. After 24 hours the vacuum was released. At which time, KOH (744.9 g) was dissolved in 90% ethanol/water (5000 mL, 90% EtOH by volume) and added to the reactor to quench the acid. The solution was then allowed to cool for approximately 30 minutes. The contents of the reactor were then pumped through a 1µ filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1µ filter back into the reactor. The reactor was heated to 60° C. in vacuo (10 torr abs) until all ethanol and water ceased to distill from solution. The remaining material was then distilled using a Myers 15 Centrifugal Distillation still at 200° C. under an absolute pressure of approximately 12 microns (0.012 torr) to remove unreacted fatty acids and leaving behind free-acid estolides (Ex. 2).

Example 3

A reactor was equipped with a mechanical stirrer, thermocouple, thermoregulator, Dean Stark trap, condenser, nitrogen sparger, and vacuum source. The reactor was charged with trimethylolpropane (TMP) (1 equiv.), the free-acid estolide product of Ex. 1 (4 equiv.), and concentrated methanesulfonic acid (0.1 equiv.). The mixture was stirred at 200-300 rpm and heated to about 100° C., and the vacuum was applied at temperature to obtain a reflux, thereby removing the water and returning the acid collected in the trap to the reactor. The temperature was maintained under vacuum for about 18-24 hrs. The reaction mixture was then cooled to rt and Amberlite IRA-402(OH) resin (water wet, 30 wt % loading with respect to free-acid estolide product) was added to the reaction mixture. Stirring was continued for an additional 18-24 hrs at rt, followed by polish filtering of the mixture over a coarse fritted funnel containing GF paper to collect the resin treated TMP estolide ester.

A reactor was charged with the resin treated TMP estolide ester and 10% Pd/C (0.16 wt %). The reactor with evacuated with nitrogen gas three times followed by hydrogen gas three times. The reactor was then sealed and placed under hydrogen pressure at 50 PSI. The reactor was heated to 60° C. and agitated at 500-900 rpm for 36-48 hrs. The reactor was then purged with nitrogen and filtered over GF paper to collect the hydrogenated TMP estolide ester. Subsequently, a reactor was purged with nitrogen and charged with the hydrogenated TMP estolide ester, followed by Amberlite IRA-402(OH) resin (16 wt % loading). The mixture was allowed to stir at ambient temperature for 18-24 hrs. The mixture was then polish filtered over a coarse fritted funnel containing Celite (20.13 g, 9.2 wt % loading) to collect the resin treated hydrogenated TMP estolide ester (186.48 g).

A reactor was charged with the resin treated hydrogenated TMP estolide ester, followed by DARCO G60 (1 wt % loading) and 4 Å molecular sieves (5 wt % loading). The mixture was agitated at 35° C. for 18-24 hrs, followed by filtration over GF paper to collect the final TMP estolide ester product.

Example 4

Polyol estolide ester are prepared according to the method set forth in Example 3, except TMP is replaced with trimethylolethane (TME) to provide a TME estolide ester product.

Example 5

Polyol estolides are prepared according to the methods set forth in Examples 3-4, except the polyol is replaced with pentaerythritol.

Example 6

Polyol estolides are prepared according to the methods set forth in Examples 3-5, except the free-acid estolide of Example 1 is replaced with the free-acid estolide product of Example 2.

Example 7

Free-acid estolides are prepared according to the method set forth in Example 1, except the oleic acid feedstock is replaced with 9-decenoic acid feedstock.

Example 8

Free-acid estolides are prepared according to the methods set forth in Example 2, except the oleic acid feedstock is replaced with 9-decenoic acid feedstock.

Example 9

Free-acid estolides are prepared according to the method set forth in Example 8, except the coconut fatty acid feedstock is replaced with acetic acid.

Example 10

Polyol estolides are independently prepared according to the methods set forth in Examples 3-6, except the free-acid estolide products of Examples 1 and 2 are independently replaced with the free-acid estolides prepared according to Examples 7, 8, and 9.

Additional Embodiments

1. At least one compound of Formula I:

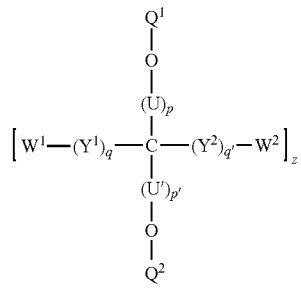

Formula I wherein
p is an integer selected from 0 to 10;
p' is an integer selected from 0 to 10;
z is an integer selected from 0 to 5;
q is, independently for each occurrence, an integer selected from 0 to 10;
q' is, independently for each occurrence, an integer selected from 0 to 10;
U is, independently for each occurrence, selected from $-C(R^3)_2-$;
U' is, independently for each occurrence, selected from $-C(R^4)_2-$;
$Y^1$ is, independently for each occurrence, selected from $-C(R^5)_2-$, $-NR^7-$, $-O-$, $-S-$, $-C(O)O-$, and $-O(O)C-$;
$Y^2$ is, independently for each occurrence, selected from $-C(R^6)_2-$, $-NR^7-$, $-O-$, $-S-$, $-C(O)O-$, and $-O(O)C-$;
$R^3$, $R^4$, $R^5$, $R^6$, and $R^7$, independently for each occurrence, are selected from hydrogen and optionally substituted alkyl that is saturated or unsaturated, and branched or unbranched;
$W^1$ is, independently for each occurrence, selected from hydrogen, optionally substituted alkyl that is saturated or unsaturated, and branched or unbranched, and $-O-Q^3$;
$W^2$ is, independently for each occurrence, selected from hydrogen, optionally substituted alkyl that is saturated or unsaturated, and branched or unbranched, and $-O-Q^4$; and
$Q_1$, $Q_2$, $Q_3$, and $Q_4$, independently for each occurrence, are selected from hydrogen and residues represented by Formula II:

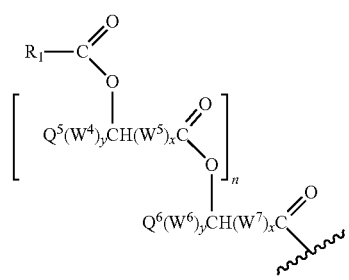

Formula II wherein
x is, independently for each occurrence, an integer selected from 0 to 20;

y is, independently for each occurrence, an integer selected from 0 to 20;
n is 0 or greater than 0;
$Q^5$ and $Q^6$, independently for each occurrence, are selected from hydrogen and —$CH_3$;
$R_1$ is, independently for each occurrence, selected from optionally substituted alkyl that is saturated or unsaturated, and branched or unbranched; and
$W^4$, $W^5$, $W^6$, and $W^7$, independently for each occurrence, are selected from —$CH_2$— and —CH=CH—,
wherein at least one of $Q_1$, $Q_2$, $Q_3$, and $Q_4$ is selected from residues of Formula II, and
wherein each fatty acid chain residue of said at least one compound is independently optionally substituted.

2. The at least one compound according to claim 1, wherein
p is an integer selected from 1 to 5; and
p' is an integer selected from 0 to 5.

3. The at least one compound according to any one of claims 1-2, wherein
p is an integer selected from 1 to 3; and
p' is an integer selected from 0 to 3.

4. The at least one compound according to any one of claims 1-3, wherein
p=1 and p'=1.

5. The at least one compound according to any one of claims 1-4, wherein z is an integer selected from 0 to 3.

6. The at least one compound according to any one of claims 1-5, wherein z=1.

7. The at least one compound according to any one of claims 1-5, wherein z=0.

8. The at least one compound according to any one of claims 1-7, wherein
q is, independently for each occurrence, an integer selected from 0 to 5; and
q' is, independently for each occurrence, an integer selected from 0 to 5.

9. The at least one compound according to any one of claims 1-8, wherein
q is, independently for each occurrence, an integer selected from 0 to 3; and
q' is, independently for each occurrence, an integer selected from 0 to 3.

10. The at least one compound according to any one of claims 1-9, wherein
q is, independently for each occurrence, an integer selected from 1 and 2, and q'=1.

11. The at least one compound according to any one of claims 1-10, wherein $R^3$, $R^4$, $R^5$, $R^6$, and $R_7$ are hydrogen for each occurrence.

12. The at least one compound according to any one of claims 1-11, wherein $W^1$ is and $W_2$ are hydrogen for each occurrence.

13. The at least one compound according to any one of claims 1-11, wherein $W^1$ and $W^2$, independently for each occurrence, are selected from hydrogen and optionally substituted alkyl that is saturated or unsaturated, and branched or unbranched.

14. The at least one compound according to any one of claims 1-11, wherein $W^1$ and $W^2$, independently for each occurrence, are selected from —O-$Q^3$ and —O-$Q^4$, respectively.

15. The at least one compound according to any one of claims 1-11, wherein $W^1$, independently for each occurrence, is selected from hydrogen and optionally substituted alkyl that is saturated or unsaturated, and branched or unbranched; and
$W^2$, independently for each occurrence, is selected from —O-$Q^4$.

16. The at least one compounds according to any one of claims 1-15, wherein $Y^1$ and $Y^2$ are —$CH_2$—.

17. The at least one compounds according to any one of claims 1-16, wherein U and U' are —$CH_2$—.

18. The at least one compound according to claim 1, wherein said at least one compound is selected from compounds of Formula III:

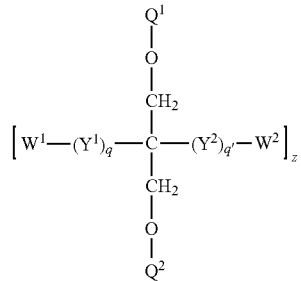

Formula III

19. The at least one compound according to claim 18, wherein
z is an integer selected from 0 to 4;
q is an integer selected from 0 to 5; and
q' is an integer selected from 0 to 5.

20. The at least one compounds according to any one of claims 18-19, wherein z is 1.

21. The at least one compound according to any one of claims 18-20, wherein
z is 1;
q is an integer selected from 0 to 2; and
q' is an integer selected from 0 to 2.

22. The at least one compound according to any one of claims 18-21, wherein
q is 1; and
q' is 1.

23. The at least one compound according to any one of claims 18-21, wherein
q is 2; and
q' is 1.

24. The at least one compounds according to any one of claims 18-23, wherein $Y^1$ and $Y^2$ are —$CH_2$—.

25. The at least one compound according to any one of claims 18-24, wherein $W^1$ and $W^2$, independently for each occurrence, are selected from hydrogen and optionally substituted alkyl that is saturated or unsaturated, and branched or unbranched.

26. The at least one compound according to any one of claims 18-24, wherein
$W^1$ is, independently for each occurrence, selected from hydrogen and optionally substituted alkyl that is saturated or unsaturated, and branched or unbranched; and
$W^2$ is, independently for each occurrence, selected from —O-$Q^4$.

27. The at least one compound according to any one of claims 18-24, wherein
$W^1$ is, independently for each occurrence, selected from —O-$Q^3$; and $W^2$ is, independently for each occurrence, selected from —O-$Q^4$.

28. The at least one compound according to any one of claims 18-26, wherein $W^1$ is hydrogen.

29. The at least one compound according to any one of claims 18-25, wherein $W^2$ is hydrogen.

30. The at least one compound according to claim 1, wherein said at least one compound is selected from compounds of Formula IV:

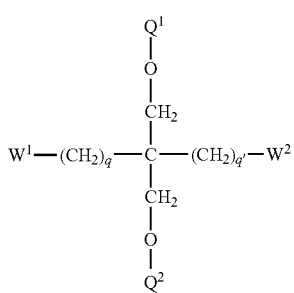

Formula IV

31. The at least one compound according to claim 30, wherein
$W^1$ is selected from hydrogen and —O-$Q^3$;
$W^2$ is selected from hydrogen and —O-$Q^4$;
q is an integer selected from 0 to 2; and
q' is an integer selected from 0 to 2.

32. The at least one compound according to claim 30, wherein
$W^1$ and $W^2$ are hydrogen;
q is an integer selected from 1 and 2; and
q' is an integer selected from 1 and 2.

33. The at least one compound according to claim 30, wherein
$W^1$ is selected from hydrogen and —O-$Q^3$;
$W^2$ is —O-$Q^4$;
q is an integer selected from 1 and 2; and
q' is an integer selected from 1 and 2.

34. The at least one compound according to claim 30, wherein $W^1$ is —O-$Q^3$.

35. The at least one compound according to claim 30, wherein $W^1$ is hydrogen.

36. The at least one compound according to any one of claims 30-35, wherein q is 2.

37. The at least one compound according to any one of claims 30-35, wherein q is 1.

38. The at least one compound according to any one of claims 30-37, wherein q' is 1.

39. The at least one compound according to any one of claims 1-38, wherein $W^4$, $W^5$, $W^6$, and $W^7$ for each occurrence are —$CH_2$—.

40. The at least one compound according to any one of claims 1-39, wherein $Q^5$ and $Q^6$ are hydrogen.

41. The at least one compound according to any one of claims 1-39, wherein $Q^5$ and $Q^6$ are —$CH_3$.

42. The at least one compound according to any one of claims 1-39, wherein $Q^5$ is hydrogen.

43. The at least one compound according to any one of claims 1-39, wherein $Q^6$ is hydrogen.

44. The at least one compound according to any one of claims 1-39, wherein $Q^5$ is —$CH_3$.

45. The at least one compound according to any one of claims 1-39, wherein $Q^6$ is —$CH_3$.

46. The at least one compound according to any one of claims 1-45, wherein at least one of $Q_1$, $Q_2$, $Q_3$, and $Q_4$ is hydrogen.

47. The at least one compound according to any one of claims 1-45, wherein $Q_1$, $Q_2$, $Q_3$, and $Q_4$, independently for each occurrence, are selected from residues of Formula II.

48. The at least one compound according to any one of claims 1-47, wherein
n is an integer selected from 0 to 8;
$R_1$ is an optionally substituted $C_1$ to $C_{22}$ alkyl that is saturated or unsaturated, and branched or unbranched; and
$R_2$ is an optionally substituted $C_1$ to $C_{22}$ alkyl that is saturated or unsaturated, and branched or unbranched,
wherein each fatty acid chain residue is unsubstituted.

49. The at least one compound according to any one of claims 1-48, wherein
x+y is, independently for each chain, an integer selected from 13 to 15; and
n is an integer selected from 0 to 6.

50. The at least one compound according to any one of claims 1-49, wherein $R_1$ is unsubstituted.

51. The at least one compound according to any one of claims 1-50, wherein $R_1$ is saturated.

52. The at least one compound according to any one of claims 1-51, wherein $R_1$ is a branched or unbranched $C_1$ to $C_{20}$ alkyl that is saturated or unsaturated.

53. The at least one compound according to any one of claims 1-52, wherein $R_1$ is selected from methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, and icosanyl.

54. The at least one compound according to any one of claims 1-49, wherein $R_1$ is selected from unsubstituted $C_7$ to $C_{17}$ alkyl that is unbranched and saturated or unsaturated.

55. The at least one compound according to any one of claims 1-49, wherein $R_1$ is selected from $C_{13}$ to $C_{17}$ alkyl that is unsubstituted, unbranched, and saturated or unsaturated.

56. The at least one compound according to claim 54, wherein $R_1$ is selected from saturated $C_7$ alkyl, saturated $C_9$ alkyl, saturated $C_{11}$ alkyl, saturated $C_{13}$ alkyl, saturated $C_{15}$ alkyl, and saturated or unsaturated $C_{17}$ alkyl, which are unsubstituted and unbranched.

57. The at least one compound according to claim 55, wherein $R_1$ is selected from saturated $C_{13}$ alkyl, saturated $C_{15}$ alkyl, and saturated or unsaturated $C_{17}$ alkyl, which are unsubstituted and unbranched.

58. The at least one compound according to any one of claims 1-57, wherein n=0

59. The at least one compound of claim 1, wherein said least one compound is selected from compounds of Formula V:

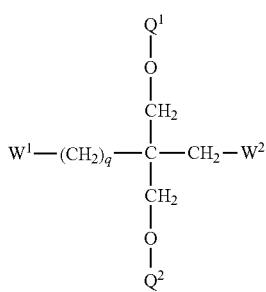

Formula V wherein q is, independently for each occurrence, an integer selected from 1 and 2;

$W^1$ is, independently for each occurrence, selected from hydrogen, optionally substituted alkyl that is saturated or unsaturated, and branched or unbranched, and —O-$Q^3$;

$W^2$ is, independently for each occurrence, selected from hydrogen, optionally substituted alkyl that is saturated or unsaturated, and branched or unbranched, and —O-$Q^4$; and $Q_1$, $Q_2$, $Q_3$, and $Q_4$, independently for each occurrence, are selected from hydrogen and substituents represented by Formula VI:

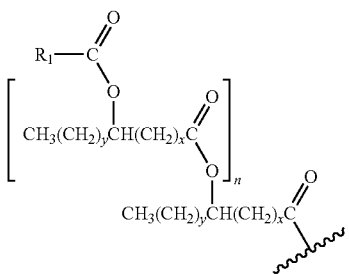

Formula VI wherein x is, independently for each occurrence, an integer selected from 1 to 10;

y is, independently for each occurrence, an integer selected from 1 to 10;

n is 0 or greater than 0;

$R_1$ is, independently for each occurrence, selected from optionally substituted alkyl that is saturated or unsaturated, and branched or unbranched; and wherein at least one of $Q_1$, $Q_2$, $Q_3$, and $Q_4$ is selected from residues of Formula VI, and wherein each fatty acid chain residue of said at least one compound is independently optionally substituted.

60. The at least one compound according to claim 59, wherein $Q_1$, $Q_2$, $Q_3$, and $Q_4$ independently for each occurrence are selected from residues of Formula VI.

61. The at least one compound according to any one of claims 59-60, wherein x+y is, independently for each chain, an integer selected from 13 to 15; and n is an integer selected from 0 to 6.

62. The at least one compound according to any one of claims 59-61, wherein x is, independently for each chain, an integer selected from 7 and 8; and y is, independently for each chain, an integer selected from 7 and 8.

63. The at least one compound according to any one of claims 59-62, wherein n is 0.

64. The at least one compound according to any one of claims 59-63, wherein $R_1$ is unsubstituted.

65. The at least one compound according to any one of claims 59-64, wherein $R_1$ is saturated.

66. The at least one compound according to any one of claims 59-63, wherein $R_1$ is a branched or unbranched $C_1$ to $C_{20}$ alkyl that is saturated or unsaturated.

67. The at least one compound according to claim 66, wherein $R_1$ is selected from methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, and icosanyl, which are saturated or unsaturated and branched or unbranched.

68. The at least one compound according to any one of claims 59-67, wherein $W^1$ is —O-$Q^3$.

69. The at least one compound according to any one of claims 59-67, wherein $W^1$ is hydrogen.

70. The at least one compound according to any one of claims 59-69, wherein $W^2$ is hydrogen.

71. The at least one compound according to any one of claims 59-69, wherein $W^2$ is —O-$Q^4$.

72. The at least one compound according to any one of claims 59-71, wherein q=1.

73. The at least one compound according to any one of claims 59-71, wherein q=2.

74. The at least one compound according to any one of claims 1-73, wherein x is, independently for each occurrence, an integer selected from 1 to 10; and y is, independently for each occurrence, an integer selected from 1 to 10.

75. The at least one compound according to any one of claims 1-73, wherein x+y is an integer selected from 13 to 15.

76. The at least one compound according to any one of claims 1-73, wherein x is, independently for each occurrence, an integer selected from 7 and 8.

77. The at least one compound according to any one of claims 1-73 and 76, wherein y is 0.

78. The at least one compound according to any one of claims 1-73 and 76, wherein y is an integer selected from 7 and 8.

79. The at least one compound according to any one of claims 59-67, wherein $W^2$ is —O-$Q^4$;

$W^1$ is hydrogen;

x is, independently for each chain, an integer selected from 7 and 8;

y is, independently for each chain, an integer selected from 7 and 8;

n=0; and $R_1$ is a branched or unbranched $C_1$ to $C_{20}$ alkyl that is saturated and unsubstituted, wherein each fatty acid chain residue is unsubstituted.

80. A method of preparing a polyol estolide compound, comprising providing at least one polyol and at least one estolide compound; and contacting the at least one polyol with the at least one estolide compound to provide the polyol estolide compound.

81. The method according to claim 80, wherein the at least one polyol comprises at least two hydroxy residues.

82. The method according to claim 80, wherein the at least one polyol comprises at least three hydroxy residues.

83. The method according to any one of claims 80-82, wherein the at least one polyol is selected from one or more of trimethylolpropane, trimethylolethane, pentaerythritol, and neopentylglycol.

84. The method according to any one of claims 80-83, wherein the at least one estolide compound is a free acid estolide.

85. The method according to any one of claims 80-83, wherein the at least one estolide compound is an estolide ester.

86. The method according to any one of claims 80-85, wherein the contacting the at least one polyol with the at least one estolide compound occurs in the presence of a catalyst.

87. The method according to claim 86, wherein the catalyst is selected from one or more of a Bronsted acid or a Lewis acid.

88. The method according to any one of claims 80-87, wherein contacting the at least one polyol with the at least one estolide compound occurs in the presence of dielectric heating.

89. The method according to claim 88, wherein contacting the at least one polyol with the at least one estolide compound occurs in the presence of microwave radiation.

90. The method according to any one of claims 75-84, wherein the polyol estolide compound comprises at least one compound according to any one of claims 1-79.

91. The method according to any one of claims 80-90, wherein the at least one estolide compound is derived from at least one metathesized fatty acid and/or metathesized fatty acid ester.

92. The method according to any one of claims 80-90, wherein the at least one estolide compound is derived from 9-decenoic acid, 9-dodecenoic acid, 10-undecenoic acid, or esters thereof.

93. At least one compound of Formula V:

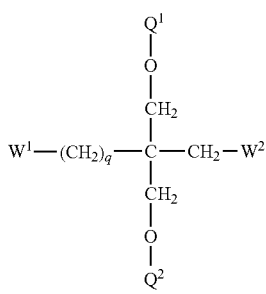

Formula V wherein
q is an integer selected from 1 and 2;
$W^1$ is, independently for each occurrence, selected from hydrogen, optionally substituted alkyl that is saturated or unsaturated, and branched or unbranched, and —O-$Q^3$;

$W^2$ is, independently for each occurrence, selected from hydrogen, optionally substituted alkyl that is saturated or unsaturated, and branched or unbranched, and —O-$Q^4$; and $Q_1$, $Q_2$, $Q_3$, and $Q_4$, independently for each occurrence, are selected from hydrogen and residues represented by Formula II:

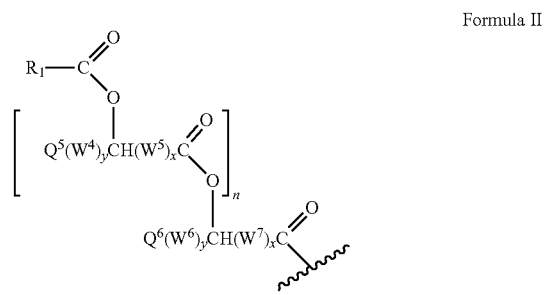

Formula II wherein
x is, independently for each occurrence, an integer selected from 0 to 20;
y is 0 for each occurrence;
n is 0 or greater than 0;
$Q^5$ and $Q^6$, independently for each occurrence, are selected from hydrogen and —$CH_3$;
$R_1$ is, independently for each occurrence, selected from optionally substituted alkyl that is saturated or unsaturated, and branched or unbranched;
$W^4$, $W^5$, $W^6$, and $W^7$, independently for each occurrence, are selected from —$CH_2$— and —CH=CH—, and
$Q^5$ and $Q^6$, independently for each occurrence, are selected from hydrogen and —$CH_3$,
wherein at least one of $Q_1$, $Q_2$, $Q_3$, and $Q_4$ is selected from residues of Formula II, and
wherein each fatty acid chain residue of said at least one compound is independently optionally substituted.

94. The at least one compound according to claim 93, wherein $Q_1$, $Q_2$, $Q_3$, and $Q_4$ independently for each occurrence are selected from residues of Formula II.

95. The at least one compound according to any one of claims 93-94, wherein n is an integer selected from 0 to 6.

96. The at least one compound according to any one of claims 93-95, wherein
x is, independently for each chain, an integer selected from 7 and 8.

97. The at least one compound according to any one of claims 93-96, wherein n is 0.

98. The at least one compound according to any one of claims 93-97, wherein $R_1$ is unsubstituted.

99. The at least one compound according to any one of claims 93-98, wherein $R_1$ is saturated.

100. The at least one compound according to any one of claims 93-99, wherein $R_1$ is a branched or unbranched $C_1$ to $C_{20}$ alkyl that is saturated or unsaturated.

101. The at least one compound according to claim 100, wherein $R_1$ is selected from methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, and icosanyl, which are saturated or unsaturated and branched or unbranched.

102. The at least one compound according to claim 101, wherein $R_1$ is selected from methyl, ethyl, propyl, butyl, pentyl, hexyl, heptyl, octyl, nonyl, and decanyl, which are saturated or unsaturated and branched or unbranched.

103. The at least one compound according to claim 101, wherein $R_1$ is methyl.

104. The at least one compound according to any one of claims 93-103, wherein $W^1$ is —O-$Q^3$ 105. The at least one compound according to any one of claims 93-104, wherein $W^1$ is hydrogen.

106. The at least one compound according to any one of claims 93-105, wherein $W^2$ is hydrogen.

107. The at least one compound according to any one of claims 93-105, wherein $W^2$ is —O-$Q^4$ 108. The at least one compound according to any one of claims 93-107, wherein q=1.

109. The at least one compound according to any one of claims 93-107, wherein q=2.

110. The at least one compound according to any one of claims 93-103, wherein
$W^2$ is —O-$Q^4$;
$W^1$ is hydrogen;
$W^5$ and $W^7$ are —$CH_2$— for each occurrence;
x is, independently for each chain, an integer selected from 7 and 8;
n=0; and
$R_1$ is a branched or unbranched $C_1$ to $C_{20}$ alkyl that is saturated and unsubstituted,
wherein each fatty acid chain residue is unsubstituted.

111. The at least one compound according to claim 110, wherein $R_1$ is selected from methyl, ethyl, propyl, butyl, pentyl, hexyl, heptyl, octyl, nonyl, and decanyl.

112. The at least one compound according to claim 110, wherein $R_1$ is methyl.

113. The at least one compound according to any one of claims 110-112, wherein $Q^5$ and $Q^6$ are —$CH_3$ for each occurrence.

114. The at least one compound according to claim 13, wherein $W^1$ and $W^2$, independently for each occurrence, are selected from optionally substituted $C_1$ to $C_{20}$ alkyl that is saturated or unsaturated, and branched or unbranched.

115. The at least one compound according to any one of claims 1-10, wherein $R^3$, $R^4$, $R^5$, $R^6$, and $R^7$ are independently selected from hydrogen and $C_1$-$C_{20}$ alkyl.

The invention claimed is:

1. A composition comprising at least one saturated polyol estolide compound, wherein the at least one saturated polyol estolide compound exhibits a hydroxyl value of greater than or equal to 40 mg KOH/g, wherein the at least one saturated polyol estolide compound is selected from compounds of Formula I:

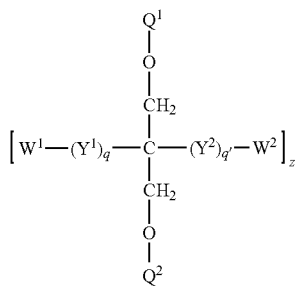

Formula III wherein
p is selected from 0 to 10;
p' is selected from 0 to 10;
z is selected from 0 to 5;
q is, independently for each occurrence, selected from 0 to 10;
q' is, independently for each occurrence, selected from 0 to 10;
U is, independently for each occurrence, selected from —C($R^3$)$_2$—;
U' is, independently for each occurrence, selected from —C($R^4$)$_2$—;
$Y^1$ is, independently for each occurrence, selected from —C($R^5$)$_2$—, —$NR^7$—, —O—, —S—, —C(O)O—, and —O(O)C—;
$Y^2$ is, independently for each occurrence, selected —C($R^6$)$_2$—, —$NR^7$—, —O—, —S—, —C(O)O—, and —O(O)C—;
$R^3$, $R^4$, $R^5$, $R^6$, and $R^7$, independently for each occurrence, are selected from hydrogen and optionally substituted alkyl that is saturated and branched or unbranched;
$W^1$ is, independently for each occurrence, selected from hydrogen, optionally substituted alkyl that is saturated and branched or unbranched, and —O-$Q^3$,
$W^2$ is, independently for each occurrence, selected from hydrogen, optionally substituted alkyl that is saturated and branched or unbranched, and —O-$Q^4$; and
$Q^1$, $Q^2$, $Q^3$, and $Q^4$, independently for each occurrence, are selected from residues represented by Formula II:

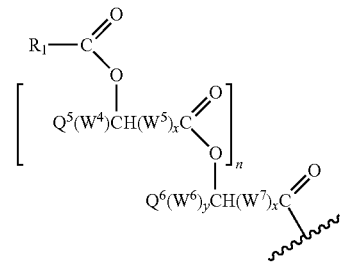

Formula II wherein
x is, independently for each occurrence, an integer selected from 0 to 20;
y is, independently for each occurrence, an integer selected from 0 to 20;
n is 0 to 20;
$Q^5$ and $Q^6$, independently for each occurrence, are selected from hydrogen and —$CH_3$;
$R_1$ is selected from saturated $C_1$ to $C_{20}$ alkyl that is branched or unbranched, and is optionally substituted; and
$W^4$, $W^5$, $W^6$, and $W^7$ are —$CH_2$— for each occurrence,
wherein each fatty acid chain residue of said at least one estolide compound is independently optionally substituted.

2. The composition of claim 1, wherein the at least one saturated polyol estolide compound is selected from compounds of Formula IV:

9. A compound is selected from Formula IV:

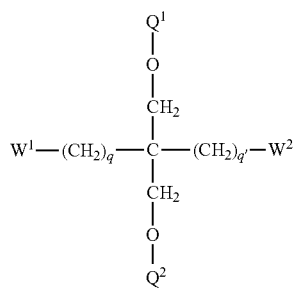
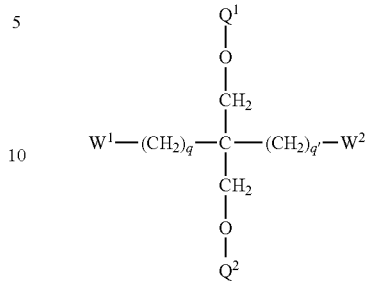

Formula IV wherein
q is 0;
q' is 0;
$W^1$ is hydrogen;
$W^2$ is —O-$Q^4$, wherein $Q^4$ is hydrogen;
$Q^2$ is hydrogen; and
$Q^1$ is a residue selected from Formula II:

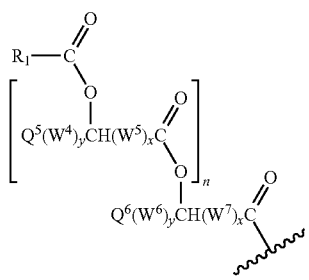
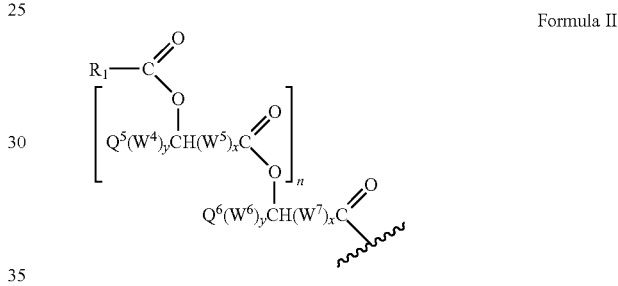

Formula II wherein
x is, independently for each occurrence, an integer selected from 0 to 20;
y is, independently for each occurrence, an integer selected from 0 to 20;
n is 0 to 20;
$Q^5$ and $Q^6$, independently for each occurrence, are selected from hydrogen and —$CH_3$;
$R_1$ is selected from saturated $C_1$ to $C_{20}$ alkyl that is branched or unbranched, and is optionally substituted; and
$W^4$, $W^5$, $W^6$, and $W^7$ are —$CH_2$— for each occurrence,
wherein each fatty acid chain residue is independently optionally substituted with one or more hydroxyl groups.

10. The composition of claim 9, wherein x is selected from 7 and 8 for each occurrence.

11. The composition of claim 10, wherein y is selected from 7 and 8 for each occurrence.

12. The composition according to claim 11, wherein $Q^5$ and $Q^6$ are —$CH_3$.

13. The composition according to claim 12, wherein n is selected from 0 to 8.

14. The composition according to claim 12, wherein n is selected from 1 to 12.

15. The composition according to claim 12, wherein $R_1$ is substituted with at least one hydroxyl group.

\* \* \* \* \*

---

(Left column:)

wherein
q is 0;
q' is 0;
$W^1$ is hydrogen;
$W^2$ is —O-$Q^4$, wherein $Q^4$ is hydrogen;
$Q^2$ is hydrogen; and
$Q^1$ is a residue selected from Formula II:

wherein
x is, independently for each occurrence, an integer selected from 0 to 20;
y is, independently for each occurrence, an integer selected from 0 to 20;
n is 0 to 20;
$Q^5$ and $Q^6$, independently for each occurrence, are selected from hydrogen and —$CH_3$;
$R_1$ is selected from saturated $C_1$ to $C_{20}$ alkyl that is branched or unbranched, and is optionally substituted; and
$W^4$, $W^5$, $W^6$, and $W^7$ are —$CH_2$— for each occurrence,
wherein each fatty acid chain residue of said at least one estolide compound is independently optionally substituted.

3. The composition of claim 2, wherein x is selected from 7 and 8 for each occurrence.

4. The composition of claim 2, wherein y is selected from 7 and 8 for each occurrence.

5. The composition according to claim 4, wherein $Q^5$ and $Q^6$ are —$CH_3$.

6. The composition according to claim 5, wherein n is selected from 0 to 8.

7. The composition according to claim 5, wherein n is selected from 1 to 12.

8. The composition according to claim 5, wherein $R_1$ is substituted with at least one hydroxyl group.